(12) United States Patent
Morris

(10) Patent No.: US 11,051,861 B2
(45) Date of Patent: *Jul. 6, 2021

(54) ROD REDUCTION ASSEMBLIES AND RELATED METHODS

(71) Applicant: Nuvasive, Inc., San Diego, CA (US)

(72) Inventor: Andrew Morris, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/007,861

(22) Filed: Jun. 13, 2018

(65) Prior Publication Data

US 2019/0380750 A1 Dec. 19, 2019

(51) Int. Cl.
*A61B 17/70* (2006.01)
*A61B 17/00* (2006.01)

(52) U.S. Cl.
CPC ............... *A61B 17/7086* (2013.01); *A61B 2017/00367* (2013.01); *A61B 2017/00477* (2013.01)

(58) Field of Classification Search
CPC ............ A61B 17/7086; A61B 17/7076; A61B 17/7085; A61B 17/7032; A61B 17/7074; A61B 17/077; A61B 17/7079; A61B 17/708; A61B 17/7091; A61B 17/7083; A61B 17/7088; A61B 17/7089; A61B 17/7082; A61B 2017/00367; A61B 2017/00477
USPC .................... 606/86 A, 246–289, 96, 99, 100
See application file for complete search history.

(56) References Cited

U.S. PATENT DOCUMENTS

| | | | |
|---|---|---|---|
| 929,067 | A | 7/1909 | Williamson |
| 4,282,217 | A | 8/1981 | Baglioni |
| 4,316,169 | A | 2/1982 | Teranishi |
| 4,450,899 | A | 5/1984 | Jakobsson |
| 4,927,425 | A | 5/1990 | Lozier |
| 4,955,885 | A | 9/1990 | Meyers |
| 5,020,519 | A | 6/1991 | Hayes |
| 5,217,497 | A | 6/1993 | Mehdian |
| D346,217 | S | 4/1994 | Sparker |
| 5,360,431 | A | 11/1994 | Puno |
| 5,474,555 | A | 12/1995 | Puno |
| 5,496,321 | A | 3/1996 | Puno |
| 5,616,143 | A | 4/1997 | Schlapfer |
| 5,624,442 | A | 4/1997 | Mellinger |
| 5,681,319 | A | 10/1997 | Biedermann |
| 5,716,356 | A | 2/1998 | Biedermann |
| 5,720,751 | A | 2/1998 | Jackson |

(Continued)

FOREIGN PATENT DOCUMENTS

| | | |
|---|---|---|
| CN | 101103935 A | 1/2008 |
| CN | 201328875 Y | 10/2009 |

(Continued)

*Primary Examiner* — Pedro Philogene
(74) *Attorney, Agent, or Firm* — NuVasive, Inc.

(57) ABSTRACT

This disclosure describes example embodiments of rod reduction instrumentation and other rod and vertebrae manipulation instruments. The rod reducers can be used during the installation of a rod based surgical fixation system to help urge the rod into the fixation anchors. The reducers described provide various configurations delivering large reduction distance capabilities, strong controlled reduction coupled with an ability to quickly advance the reducer if desired, and reduction of bulk through the surgical corridor.

20 Claims, 7 Drawing Sheets

(56) References Cited

U.S. PATENT DOCUMENTS

| | | |
|---|---|---|
| 5,782,831 A | 7/1998 | Sherman |
| 5,782,833 A | 7/1998 | Haider |
| 5,810,878 A | 9/1998 | Burel |
| 5,910,141 A | 6/1999 | Morrison |
| 5,941,885 A | 8/1999 | Jackson |
| 5,944,720 A | 8/1999 | Lipton |
| 6,004,349 A | 12/1999 | Jackson |
| 6,059,786 A | 5/2000 | Jackson |
| 6,123,707 A | 9/2000 | Wagner |
| 6,139,549 A | 10/2000 | Waldemar |
| 6,179,841 B1 | 1/2001 | Jackson |
| 6,183,472 B1 | 2/2001 | Lutz |
| 6,189,422 B1 | 2/2001 | Stihl |
| 6,224,598 B1 | 5/2001 | Jackson |
| 6,248,107 B1 | 6/2001 | Foley |
| 6,251,111 B1 | 6/2001 | Barker |
| 6,251,112 B1 | 6/2001 | Jackson |
| 6,258,090 B1 | 7/2001 | Jackson |
| 6,379,356 B1 | 4/2002 | Jackson |
| 6,440,132 B1 | 8/2002 | Jackson |
| 6,440,133 B1 | 8/2002 | Beale |
| 6,485,494 B1 | 11/2002 | Haider |
| 6,520,963 B1 | 2/2003 | McKinley |
| 6,530,929 B1 | 3/2003 | Justis et al. |
| 6,554,834 B1 | 4/2003 | Crozet |
| 6,575,981 B1 | 6/2003 | Boyd |
| 6,648,888 B1 | 11/2003 | Shluzas |
| 6,660,006 B2 | 12/2003 | Markworth |
| 6,723,100 B2 | 4/2004 | Biedermann |
| 6,726,687 B2 | 4/2004 | Jackson |
| 6,726,692 B2 | 4/2004 | Bette |
| 6,740,089 B2 | 5/2004 | Haider |
| 6,743,231 B1 | 6/2004 | Gray |
| 6,746,449 B2 | 6/2004 | Jones |
| 6,884,244 B1 | 4/2005 | Jackson |
| 6,981,973 B2 | 1/2006 | McKinley |
| 7,008,422 B2 | 3/2006 | Foley |
| 7,011,660 B2 | 3/2006 | Sherman |
| 7,073,415 B2 | 7/2006 | Casutt |
| 7,094,239 B1 | 8/2006 | Michelson |
| 7,156,849 B2 | 1/2007 | Dunbar |
| 7,160,300 B2 | 1/2007 | Jackson |
| 7,179,261 B2 | 2/2007 | Sicvol et al. |
| 7,188,626 B2 | 3/2007 | Foley |
| 7,204,838 B2 | 4/2007 | Jackson |
| 7,250,052 B2 | 7/2007 | Landry et al. |
| 7,278,995 B2 | 10/2007 | Nichols |
| D560,128 S | 1/2008 | Diederich et al. |
| 7,371,239 B2 | 5/2008 | Dec |
| 7,462,182 B2 | 12/2008 | Lim |
| 7,470,279 B2 | 12/2008 | Jackson |
| 7,476,240 B2 | 1/2009 | Raymond |
| 7,481,813 B1 | 1/2009 | Purcell |
| 7,491,207 B2 | 2/2009 | Keyer |
| 7,491,208 B2 | 2/2009 | Pond, Jr. et al. |
| 7,491,218 B2 | 2/2009 | Landry |
| 7,520,879 B2 | 4/2009 | Justis |
| 7,527,638 B2 | 5/2009 | Anderson |
| 7,563,264 B2 | 7/2009 | Landry |
| 7,572,281 B2 | 8/2009 | Runco |
| 7,574,318 B2 | 8/2009 | Hsieh |
| 7,588,575 B2 | 9/2009 | Colleran |
| 7,588,588 B2 | 9/2009 | Spitler |
| 7,591,836 B2 | 9/2009 | Dick |
| 7,597,694 B2 | 10/2009 | Lim |
| 7,608,081 B2 | 10/2009 | Abdelgany |
| 7,611,517 B2 | 11/2009 | Lim |
| 7,618,422 B2 | 11/2009 | Goodwin |
| 7,621,918 B2 | 11/2009 | Jackson |
| 7,625,376 B2 | 12/2009 | Brumfield |
| 7,648,521 B2 | 1/2010 | Hestad |
| 7,651,502 B2 | 1/2010 | Jackson |
| 7,678,139 B2 | 3/2010 | Garamszegi |
| 7,691,132 B2 | 4/2010 | Landry |
| 7,708,743 B2 | 5/2010 | Anderson |
| 7,708,763 B2 | 5/2010 | Selover |
| 7,717,921 B2 | 5/2010 | Rezach |
| 7,717,942 B2 | 5/2010 | Schumacher |
| 7,717,944 B2 | 5/2010 | Foley |
| 7,722,617 B2 | 5/2010 | Young |
| 7,744,629 B2 | 6/2010 | Hestad |
| 7,749,233 B2 | 7/2010 | Farr |
| 7,758,617 B2 | 7/2010 | Iott et al. |
| 7,763,055 B2 | 7/2010 | Foley |
| 7,771,430 B2 | 8/2010 | Jones |
| 7,776,074 B2 | 8/2010 | Bray |
| 7,799,031 B2 | 9/2010 | Miller |
| 7,811,288 B2 | 10/2010 | Jones |
| 7,815,664 B2 | 10/2010 | Sherman |
| 7,824,413 B2 | 11/2010 | Varieur |
| 7,854,751 B2 | 12/2010 | Sicvol |
| 7,862,587 B2 | 1/2011 | Jackson |
| 7,862,595 B2 | 1/2011 | Foley |
| 7,867,259 B2 | 1/2011 | Foley |
| 7,909,835 B2 | 3/2011 | Oribe |
| 7,914,558 B2 | 3/2011 | Landry |
| 7,918,857 B2 | 4/2011 | Dziedzic |
| 7,918,858 B2 | 4/2011 | Stad |
| 7,918,878 B2 | 4/2011 | Songer |
| 7,922,727 B2 | 4/2011 | Songer |
| 7,922,749 B2 | 4/2011 | Dewey |
| 7,927,334 B2 | 4/2011 | Miller |
| 7,927,360 B2 | 4/2011 | Pond, Jr. |
| 7,931,654 B2 | 4/2011 | Jones |
| 7,931,673 B2 | 4/2011 | Hestad |
| 7,947,045 B2 | 5/2011 | Hestad |
| 7,947,046 B2 | 5/2011 | Justis |
| 7,955,355 B2 | 6/2011 | Chin |
| 7,967,821 B2 | 6/2011 | Sicvol |
| 7,985,242 B2 | 7/2011 | Forton |
| 7,988,694 B2 | 8/2011 | Barrus |
| 7,988,698 B2 | 8/2011 | Rosenberg |
| 8,002,798 B2 | 8/2011 | Chin |
| 8,025,682 B2 | 9/2011 | Mahoney |
| 8,034,084 B2 | 10/2011 | Landry |
| D649,243 S | 11/2011 | Barry et al. |
| 8,052,720 B2 | 11/2011 | Kuester |
| 8,062,340 B2 | 11/2011 | Berrevoets |
| 8,066,739 B2 | 11/2011 | Jackson |
| 8,075,592 B2 | 12/2011 | Landry |
| 8,096,996 B2 | 1/2012 | Gutierrez |
| 8,100,915 B2 | 1/2012 | Jackson |
| 8,100,951 B2 | 1/2012 | Justis |
| 8,105,361 B2 | 1/2012 | Anderson |
| 8,128,629 B2 | 3/2012 | Barry |
| 8,137,355 B2 | 3/2012 | Hestad |
| 8,137,356 B2 | 3/2012 | Hestad |
| 8,137,387 B2 | 3/2012 | Garamszegi |
| 8,142,436 B2 | 3/2012 | Kirschman |
| 8,142,437 B2 | 3/2012 | McLean |
| 8,147,524 B2 | 4/2012 | Piza Vallespir |
| 8,152,810 B2 | 4/2012 | Jackson |
| 8,162,948 B2 | 4/2012 | Jackson |
| 8,172,847 B2 | 5/2012 | Dziedzic |
| 8,177,817 B2 | 5/2012 | Fallin |
| 8,192,438 B2 | 6/2012 | Garamszegi |
| 8,192,439 B2 | 6/2012 | Songer |
| 8,192,440 B2 | 6/2012 | Jones |
| 8,197,519 B2 | 6/2012 | Schlaepfer |
| 8,206,394 B2 | 6/2012 | Stad |
| 8,211,111 B2 | 7/2012 | Dauster |
| 8,216,240 B2 | 7/2012 | Dewey |
| 8,231,635 B2 | 7/2012 | Sharifi-Mehr |
| 8,235,997 B2 | 8/2012 | Hoffman |
| 8,236,032 B2 | 8/2012 | Ramsay |
| 8,246,623 B2 | 8/2012 | Peultier |
| 8,262,662 B2 | 9/2012 | Beardsley |
| 8,273,089 B2 | 9/2012 | Jackson |
| 8,277,491 B2 | 10/2012 | Selover |
| 8,292,892 B2 | 10/2012 | Jackson |
| 8,303,595 B2 | 11/2012 | Jones |
| 8,308,728 B2 | 11/2012 | Iott |
| 8,308,729 B2 | 11/2012 | Nunley |
| 8,308,774 B2 | 11/2012 | Hoffman |

(56) References Cited

U.S. PATENT DOCUMENTS

| | | |
|---|---|---|
| 8,317,796 B2 | 11/2012 | Stihl |
| 8,361,124 B2 | 1/2013 | Sherman |
| 8,377,065 B2 | 2/2013 | Kuntz |
| 8,377,067 B2 | 2/2013 | Jackson |
| 8,388,659 B1 | 3/2013 | Lab |
| 8,439,952 B2 | 5/2013 | Geist |
| 8,449,549 B2 | 5/2013 | Barry |
| 8,454,664 B2 | 6/2013 | McLean |
| 8,460,300 B2 | 6/2013 | Hestad |
| 8,460,308 B2 | 6/2013 | Marino |
| 8,470,008 B2 | 6/2013 | Dickinson |
| 8,496,685 B2 | 7/2013 | Landry |
| 8,512,343 B2 | 8/2013 | Dziedzic |
| 8,512,344 B2 | 8/2013 | Hoffman |
| 8,518,082 B2 | 8/2013 | Sicvol |
| 8,535,318 B2 | 9/2013 | Peterson |
| 8,540,718 B2 | 9/2013 | Dauster |
| 8,545,505 B2 | 10/2013 | Sandstrom |
| 8,551,141 B2 | 10/2013 | Gephart |
| 8,556,904 B2 | 10/2013 | Rezach |
| 8,603,094 B2 | 12/2013 | Walker |
| 8,608,746 B2 | 12/2013 | Kolb |
| 8,617,165 B2 | 12/2013 | Harper |
| 8,617,427 B2 | 12/2013 | Jiang |
| RE44,813 E | 3/2014 | Beale et al. |
| 8,663,292 B2 | 3/2014 | Dec |
| 8,663,298 B2 | 3/2014 | Keyer |
| 8,672,944 B2 | 3/2014 | Boachie-Adjei |
| 8,679,128 B2 | 3/2014 | Seelig |
| 8,685,029 B2 | 4/2014 | Dziedzic |
| 8,747,409 B2 | 6/2014 | Ichelmann |
| 8,764,756 B2 | 7/2014 | Jones |
| 8,777,953 B1 | 7/2014 | Khalili |
| 8,790,348 B2 | 7/2014 | Stad |
| 8,828,006 B2 | 9/2014 | Semler |
| 8,864,767 B2 | 10/2014 | Blain |
| 8,888,819 B2 | 11/2014 | Frasier |
| 8,900,240 B2 | 12/2014 | White |
| 8,900,248 B2 | 12/2014 | Biyani |
| 8,911,442 B2 | 12/2014 | Wing |
| 8,932,296 B2 | 1/2015 | Neary |
| 8,956,360 B2 | 2/2015 | Boachie-Adjei |
| 8,961,523 B2 | 2/2015 | Barrus |
| 8,979,848 B2 | 3/2015 | Butters |
| 8,992,536 B2 | 3/2015 | Piza Vallespir |
| 8,998,958 B2 | 4/2015 | Dauster |
| 9,005,204 B2 | 4/2015 | Manninen |
| 9,005,260 B2 | 4/2015 | Dauster |
| 9,050,139 B2 | 6/2015 | Jackson |
| 9,066,763 B2 | 6/2015 | Khoo |
| 9,220,543 B2 | 12/2015 | Walker |
| 2002/0016595 A1 | 2/2002 | Michelson |
| 2002/0072750 A1 | 6/2002 | Jackson |
| 2002/0072751 A1 | 6/2002 | Jackson |
| 2002/0095153 A1 | 7/2002 | Jones |
| 2002/0133159 A1 | 9/2002 | Jackson |
| 2003/0023243 A1 | 1/2003 | Biedermann |
| 2003/0028195 A1 | 2/2003 | Bette |
| 2003/0032957 A1 | 2/2003 | McKinley |
| 2003/0187445 A1 | 10/2003 | Keith |
| 2003/0199872 A1 | 10/2003 | Markworth |
| 2003/0224327 A1 | 12/2003 | Constantino |
| 2003/0225408 A1 | 12/2003 | Nichols |
| 2003/0236529 A1 | 12/2003 | Shluzas |
| 2004/0039383 A1 | 2/2004 | Jackson |
| 2004/0049196 A1 | 3/2004 | Jackson |
| 2004/0138662 A1 | 7/2004 | Landry |
| 2004/0147936 A1 | 7/2004 | Rosenberg |
| 2004/0147937 A1 | 7/2004 | Dunbar, Jr. |
| 2004/0158247 A1 | 8/2004 | Sitiso |
| 2004/0162560 A1 | 8/2004 | Raynor |
| 2004/0167523 A1 | 8/2004 | Jackson |
| 2004/0167524 A1 | 8/2004 | Jackson |
| 2004/0167525 A1 | 8/2004 | Jackson |
| 2004/0167526 A1 | 8/2004 | Jackson |
| 2004/0254576 A1 | 12/2004 | Dunbar |
| 2004/0267275 A1 | 12/2004 | Cournoyer |
| 2005/0010220 A1 | 1/2005 | Casutt |
| 2005/0038430 A1 | 2/2005 | McKinley |
| 2005/0059969 A1 | 3/2005 | McKinley |
| 2005/0119667 A1 | 6/2005 | Leport |
| 2005/0149048 A1 | 7/2005 | Leport |
| 2005/0171540 A1 | 8/2005 | Lim |
| 2005/0176468 A1 | 8/2005 | Iacono |
| 2005/0182410 A1 | 8/2005 | Jackson |
| 2005/0187549 A1 | 8/2005 | Jackson |
| 2005/0192570 A1 | 9/2005 | Jackson |
| 2005/0192579 A1 | 9/2005 | Jackson |
| 2005/0192587 A1 | 9/2005 | Lim |
| 2005/0228380 A1 | 10/2005 | Moore |
| 2005/0228392 A1 | 10/2005 | Keyer |
| 2005/0261687 A1 | 11/2005 | Garamszegi |
| 2005/0261702 A1 | 11/2005 | Oribe |
| 2006/0009773 A1 | 1/2006 | Jackson |
| 2006/0009775 A1 | 1/2006 | Dec |
| 2006/0025768 A1 | 2/2006 | Iott |
| 2006/0025769 A1 | 2/2006 | Dick |
| 2006/0025771 A1 | 2/2006 | Jackson |
| 2006/0036254 A1 | 2/2006 | Lim |
| 2006/0036260 A1 | 2/2006 | Runco |
| 2006/0069391 A1 | 3/2006 | Jackson |
| 2006/0074418 A1 | 4/2006 | Jackson |
| 2006/0079909 A1 | 4/2006 | Runco |
| 2006/0083603 A1 | 4/2006 | Jackson |
| 2006/0089651 A1 | 4/2006 | Trudeau |
| 2006/0095035 A1 | 5/2006 | Jones |
| 2006/0100622 A1 | 5/2006 | Jackson |
| 2006/0111712 A1 | 5/2006 | Jackson |
| 2006/0111713 A1 | 5/2006 | Jackson |
| 2006/0111715 A1 | 5/2006 | Jackson |
| 2006/0111730 A1 | 5/2006 | Hay |
| 2006/0122597 A1 | 6/2006 | Jones |
| 2006/0149235 A1 | 7/2006 | Jackson |
| 2006/0149238 A1 | 7/2006 | Sherman |
| 2006/0166534 A1 | 7/2006 | Brumfield |
| 2006/0184178 A1 | 8/2006 | Jackson |
| 2006/0200132 A1 | 9/2006 | Chao |
| 2006/0229614 A1 | 10/2006 | Foley |
| 2006/0247630 A1 | 11/2006 | Iott |
| 2006/0253120 A1 | 11/2006 | Anderson |
| 2006/0264934 A1 | 11/2006 | Fallin |
| 2006/0271050 A1 | 11/2006 | Piza Vallespir |
| 2006/0276789 A1 | 12/2006 | Jackson |
| 2006/0293661 A1 | 12/2006 | Bray |
| 2006/0293684 A1 | 12/2006 | Shluzas |
| 2006/0293690 A1 | 12/2006 | Abdelgany |
| 2006/0293692 A1 | 12/2006 | Whipple |
| 2007/0032162 A1 | 2/2007 | Jackson |
| 2007/0043378 A1 | 2/2007 | Kumar |
| 2007/0055240 A1 | 3/2007 | Matthis |
| 2007/0065692 A1 | 3/2007 | Ryoo |
| 2007/0093817 A1 | 4/2007 | Barrus |
| 2007/0093849 A1 | 4/2007 | Jones |
| 2007/0129731 A1 | 6/2007 | Sicvol |
| 2007/0161998 A1 | 7/2007 | Whipple |
| 2007/0162010 A1 | 7/2007 | Chao |
| 2007/0213714 A1 | 9/2007 | Justis |
| 2007/0213722 A1 | 9/2007 | Jones |
| 2007/0233072 A1 | 10/2007 | Dickinson |
| 2007/0233097 A1 | 10/2007 | Anderson et al. |
| 2007/0255284 A1 | 11/2007 | Miller |
| 2007/0270811 A1 | 11/2007 | Dewey |
| 2007/0270868 A1 | 11/2007 | Dewey |
| 2007/0270869 A1 | 11/2007 | Young |
| 2007/0276379 A1 | 11/2007 | Miller |
| 2007/0282337 A1 | 12/2007 | Garamszegi |
| 2007/0288002 A1 | 12/2007 | Carls |
| 2007/0288007 A1 | 12/2007 | Burkus et al. |
| 2007/0299450 A1 | 12/2007 | Her |
| 2008/0009864 A1 | 1/2008 | Forton |
| 2008/0015601 A1 | 1/2008 | Castro |
| 2008/0039844 A1 | 2/2008 | Jackson |
| 2008/0039848 A1 | 2/2008 | Jackson |
| 2008/0045950 A1 | 2/2008 | Dewey |

(56) References Cited

U.S. PATENT DOCUMENTS

| | | |
|---|---|---|
| 2008/0045953 A1 | 2/2008 | Garamszegi |
| 2008/0045955 A1 | 2/2008 | Berrevoets |
| 2008/0045957 A1 | 2/2008 | Landry |
| 2008/0045970 A1 | 2/2008 | Saidha |
| 2008/0051781 A1 | 2/2008 | Geist |
| 2008/0051794 A1 | 2/2008 | Dec |
| 2008/0086132 A1 | 4/2008 | Biedermann |
| 2008/0091213 A1 | 4/2008 | Jackson |
| 2008/0119852 A1 | 5/2008 | Dalton |
| 2008/0154277 A1 | 6/2008 | MacHalk |
| 2008/0172062 A1 | 7/2008 | Donahue |
| 2008/0177269 A1 | 7/2008 | Seelig |
| 2008/0195155 A1 | 8/2008 | Hoffman |
| 2008/0221583 A1 | 9/2008 | Sharifi-Mehr |
| 2008/0221626 A1 | 9/2008 | Butters |
| 2008/0228233 A1 | 9/2008 | Hoffman |
| 2008/0234678 A1 | 9/2008 | Gutierrez |
| 2008/0234765 A1 | 9/2008 | Frasier |
| 2008/0243190 A1 | 10/2008 | Dziedzic |
| 2008/0275456 A1 | 11/2008 | Vonwiller |
| 2008/0288005 A1 | 11/2008 | Jackson |
| 2008/0300638 A1 | 12/2008 | Beardsley |
| 2008/0319477 A1 | 12/2008 | Justis |
| 2009/0012567 A1 | 1/2009 | Biedermann |
| 2009/0018593 A1 | 1/2009 | Barrus |
| 2009/0030419 A1 | 1/2009 | Runco |
| 2009/0030420 A1 | 1/2009 | Runco |
| 2009/0062858 A1 | 3/2009 | Dziedzic |
| 2009/0062859 A1 | 3/2009 | Mahoney |
| 2009/0062860 A1 | 3/2009 | Frasier |
| 2009/0088764 A1 | 4/2009 | Stad |
| 2009/0105712 A1 | 4/2009 | Dauster |
| 2009/0149887 A1 | 6/2009 | Schlaepfer |
| 2009/0157125 A1 | 6/2009 | Hoffman |
| 2009/0163956 A1 | 6/2009 | Biedermann |
| 2009/0163962 A1 | 6/2009 | Dauster |
| 2009/0174467 A1 | 7/2009 | Kim |
| 2009/0216281 A1 | 8/2009 | Vonwiller |
| 2009/0216328 A1 | 8/2009 | Birkmeyer |
| 2009/0228053 A1 | 9/2009 | Kolb |
| 2009/0228054 A1 | 9/2009 | Hoffman |
| 2009/0228055 A1 | 9/2009 | Jackson |
| 2009/0228056 A1 | 9/2009 | Jackson |
| 2009/0234395 A1 | 9/2009 | Hoffman |
| 2009/0240292 A1 | 9/2009 | Butler |
| 2009/0254125 A1 | 10/2009 | Predick |
| 2009/0275994 A1 | 11/2009 | Phan |
| 2009/0281582 A1 | 11/2009 | Villa |
| 2009/0299414 A1 | 12/2009 | Jackson |
| 2009/0306721 A1 | 12/2009 | Kirschman |
| 2010/0004696 A1 | 1/2010 | Jackson |
| 2010/0024487 A1 | 2/2010 | Khoo |
| 2010/0036432 A1 | 2/2010 | Ely |
| 2010/0036434 A1 | 2/2010 | Ely |
| 2010/0057126 A1 | 3/2010 | Hestad |
| 2010/0063552 A1 | 3/2010 | Chin |
| 2010/0121385 A1 | 5/2010 | Blain |
| 2010/0121386 A1 | 5/2010 | Peultier |
| 2010/0137875 A1 | 6/2010 | Marino |
| 2010/0137991 A1 | 6/2010 | Ainsworth |
| 2010/0160921 A1 | 6/2010 | Sun |
| 2010/0179602 A1 | 7/2010 | Dauster |
| 2010/0185248 A1 | 7/2010 | Barry |
| 2010/0198272 A1 | 8/2010 | Keyer |
| 2010/0228302 A1 | 9/2010 | Dauster |
| 2010/0238572 A1 | 9/2010 | Tao |
| 2010/0262198 A1 | 10/2010 | Braunschweiler |
| 2010/0292742 A1 | 11/2010 | Stad |
| 2010/0294595 A1 | 11/2010 | Osburn |
| 2010/0298838 A1 | 11/2010 | Walters |
| 2010/0305625 A1 | 12/2010 | Kuntz |
| 2010/0312279 A1 | 12/2010 | Gephart |
| 2010/0331901 A1 | 12/2010 | Iott |
| 2011/0004222 A1 | 1/2011 | Biedermann |
| 2011/0009910 A1 | 1/2011 | Jackson |
| 2011/0015678 A1 | 1/2011 | Jackson |
| 2011/0034961 A1 | 2/2011 | Runco |
| 2011/0034962 A1 | 2/2011 | Dunbar, Jr. |
| 2011/0040328 A1 | 2/2011 | Miller |
| 2011/0040335 A1 | 2/2011 | Stihl |
| 2011/0077692 A1 | 3/2011 | Jackson |
| 2011/0087293 A1 | 4/2011 | Ferreira |
| 2011/0087298 A1 | 4/2011 | Jones |
| 2011/0093015 A1 | 4/2011 | Ramsay |
| 2011/0106187 A1 | 5/2011 | Foley |
| 2011/0118791 A1 | 5/2011 | Nunley |
| 2011/0137358 A1 | 6/2011 | Manninen |
| 2011/0166606 A1 | 7/2011 | Stihl |
| 2011/0166610 A1 | 7/2011 | Altarac |
| 2011/0172714 A1 | 7/2011 | Boachie-Adjei |
| 2011/0184469 A1 | 7/2011 | Ballard |
| 2011/0186787 A1 | 8/2011 | Jiang |
| 2011/0202096 A1 | 8/2011 | White |
| 2011/0202137 A1 | 8/2011 | Keith |
| 2011/0218583 A1 | 9/2011 | Smith |
| 2011/0234466 A1 | 9/2011 | Yamada |
| 2011/0238117 A1 | 9/2011 | Geist |
| 2011/0257692 A1 | 10/2011 | Sandstrom |
| 2011/0263945 A1 | 10/2011 | Peterson |
| 2011/0282390 A1 | 11/2011 | Hua |
| 2011/0282402 A1 | 11/2011 | Chao |
| 2011/0313464 A1 | 12/2011 | McLean |
| 2011/0313470 A1 | 12/2011 | McLean |
| 2011/0319938 A1 | 12/2011 | Piza Vallespir |
| 2012/0016425 A1 | 1/2012 | Shaffrey |
| 2012/0022594 A1 | 1/2012 | Walker |
| 2012/0035668 A1 | 2/2012 | Manninen |
| 2012/0053643 A1 | 3/2012 | Harper |
| 2012/0078308 A1 | 3/2012 | Dziedzic |
| 2012/0078316 A1 | 3/2012 | Anderson |
| 2012/0083853 A1 | 4/2012 | Boachie-Adjei |
| 2012/0100497 A1 | 4/2012 | Joo |
| 2012/0123431 A1 | 5/2012 | Robinson |
| 2012/0123487 A1 | 5/2012 | Mahar |
| 2012/0143269 A1 | 6/2012 | Ichelmann |
| 2012/0158070 A1 | 6/2012 | Jackson |
| 2012/0165876 A1 | 6/2012 | Nichols |
| 2012/0185003 A1 | 7/2012 | Biedermann |
| 2012/0191144 A1 | 7/2012 | Peultier |
| 2012/0197318 A1 | 8/2012 | Barry |
| 2012/0203288 A1 | 8/2012 | Lange |
| 2012/0203291 A1 | 8/2012 | Boulaine |
| 2012/0215266 A1 | 8/2012 | Jones |
| 2012/0271365 A1 | 10/2012 | Daubs |
| 2012/0277800 A1 | 11/2012 | Jackson |
| 2012/0277808 A1 | 11/2012 | May |
| 2012/0283786 A1 | 11/2012 | Rezach |
| 2012/0303062 A1 | 11/2012 | Amstutz |
| 2013/0018419 A1* | 1/2013 | Rezach ............ A61B 17/7076 606/264 |
| 2013/0030445 A1 | 1/2013 | Dauster |
| 2013/0035728 A1 | 2/2013 | Jackson |
| 2013/0035729 A1 | 2/2013 | Hammer |
| 2013/0046345 A1 | 2/2013 | Jones |
| 2013/0066385 A1 | 3/2013 | Benoist |
| 2013/0066386 A1 | 3/2013 | Biedermann |
| 2013/0072987 A1 | 3/2013 | Justis |
| 2013/0079827 A1 | 3/2013 | Neary |
| 2013/0085536 A1 | 4/2013 | Biedermann |
| 2013/0090697 A1 | 4/2013 | George |
| 2013/0103094 A1 | 4/2013 | Beale |
| 2013/0103096 A1 | 4/2013 | Miller |
| 2013/0110124 A1 | 5/2013 | Gleason |
| 2013/0110184 A1 | 5/2013 | Wing |
| 2013/0184763 A1 | 7/2013 | McClintock |
| 2013/0190822 A1 | 7/2013 | Rezach |
| 2013/0245692 A1 | 9/2013 | Hayes |
| 2013/0253598 A1 | 9/2013 | Jackson |
| 2013/0296949 A1 | 11/2013 | Sicvol |
| 2013/0296950 A1 | 11/2013 | Landry |
| 2013/0304130 A1 | 11/2013 | Jackson |
| 2013/0345759 A1 | 12/2013 | Meyer |
| 2014/0031872 A1 | 1/2014 | Jackson |
| 2014/0031873 A1 | 1/2014 | Jackson |

(56) References Cited

U.S. PATENT DOCUMENTS

| | | |
|---|---|---|
| 2014/0039567 A1 | 2/2014 | Hoefer |
| 2014/0052197 A1* | 2/2014 | McBride ............ A61B 17/7085 606/86 A |
| 2014/0058464 A1 | 2/2014 | Hutchens |
| 2014/0058465 A1 | 2/2014 | Nichols |
| 2014/0074105 A1 | 3/2014 | Peultier |
| 2014/0074106 A1 | 3/2014 | Shin |
| 2014/0100613 A1 | 4/2014 | Iott et al. |
| 2014/0100617 A1 | 4/2014 | Sandstrom |
| 2014/0100618 A1 | 4/2014 | Kolb |
| 2014/0107708 A1 | 4/2014 | Biedermann |
| 2014/0148865 A1 | 5/2014 | Hennard |
| 2014/0163625 A1 | 6/2014 | Meyer |
| 2014/0194939 A1 | 7/2014 | Seelig |
| 2014/0214084 A1 | 7/2014 | Jackson |
| 2014/0214097 A1 | 7/2014 | Jackson et al. |
| 2015/0066042 A1 | 3/2015 | Cummins |
| 2015/0066084 A1 | 3/2015 | Petit |
| 2015/0142060 A1 | 5/2015 | Jackson |
| 2017/0143385 A1* | 5/2017 | Biyani ............... A61B 17/7086 |
| 2017/0252074 A1* | 9/2017 | Semingson ........ A61B 17/7085 |
| 2019/0183542 A1* | 6/2019 | Lish .................. A61B 17/7086 |

FOREIGN PATENT DOCUMENTS

| | | |
|---|---|---|
| CN | 201684006 U | 12/2010 |
| CN | 101732086 A | 6/2011 |
| CN | 202044328 U | 11/2011 |
| CN | 202146354 U | 2/2012 |
| CN | 202342173 U | 7/2012 |
| DE | 4238339 C2 | 10/1994 |
| DE | 202011102890 U1 | 11/2011 |
| DE | 202012102895 U1 | 8/2012 |
| DE | 102011103252 A1 | 11/2012 |
| EP | 1839606 | 11/2008 |
| EP | 2324787 A1 | 5/2011 |
| EP | 2070485 B1 | 9/2011 |
| EP | 2462889 B1 | 8/2013 |
| EP | 1891904 B1 | 12/2013 |
| EP | 2574297 B1 | 11/2015 |
| EP | 2719347 B1 | 12/2016 |
| FR | 2677242 A1 | 12/1992 |
| FR | 2801492 B1 | 1/2003 |
| FR | 2920663 B1 | 8/2010 |
| FR | 2935093 B1 | 3/2011 |
| FR | 2985166 B1 | 5/2015 |
| JP | H0956736 A | 3/1997 |
| JP | 2003265492 A | 9/2003 |
| JP | 2007298123 A | 11/2007 |
| KR | 20080035999 A | 4/2008 |
| KR | 20140035296 A | 3/2014 |
| RU | 2009136963 A | 4/2011 |
| RU | 2010108859 A | 9/2011 |
| WO | 1996021396 A1 | 7/1996 |
| WO | 2002094114 A1 | 11/2002 |
| WO | 2005055843 A1 | 6/2005 |
| WO | 2005058141 A2 | 6/2005 |
| WO | 2005063135 A1 | 7/2005 |
| WO | 2007013059 A2 | 2/2007 |
| WO | 2010024787 A1 | 3/2010 |
| WO | 2010054079 A2 | 5/2010 |
| WO | 2011133160 A1 | 10/2011 |
| WO | 2012127267 A1 | 9/2012 |
| WO | 2012127268 A1 | 9/2012 |
| WO | 2013019873 A1 | 2/2013 |
| WO | 2013112689 A2 | 8/2013 |
| WO | 2013150232 A1 | 10/2013 |
| WO | 2013187928 A1 | 12/2013 |
| WO | 2014013203 A1 | 1/2014 |

* cited by examiner

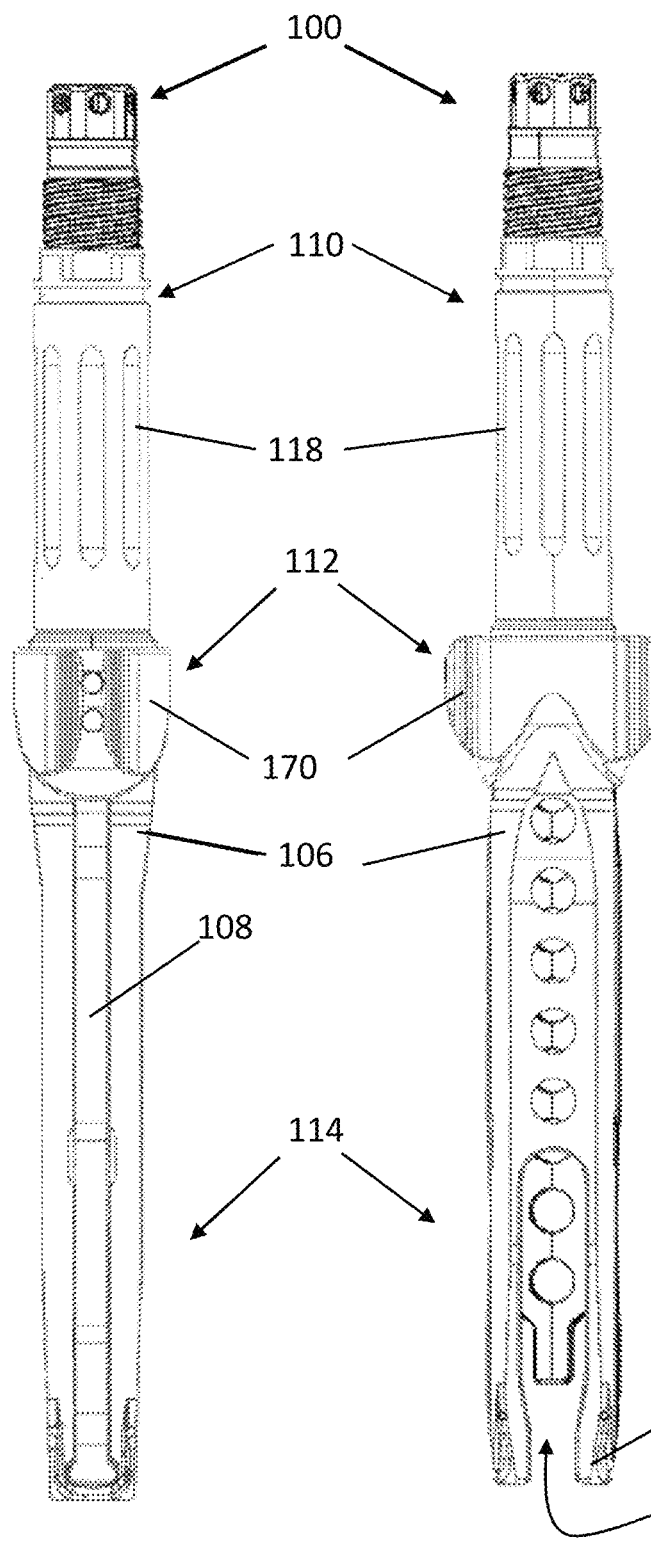
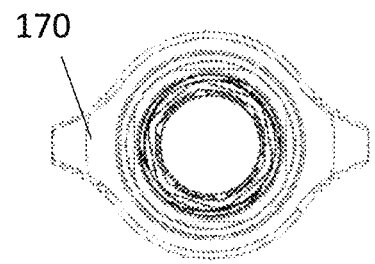
FIG. 5
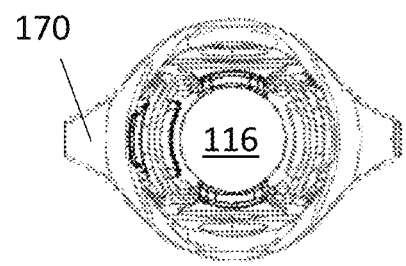
FIG. 6
FIG. 3　　FIG. 4

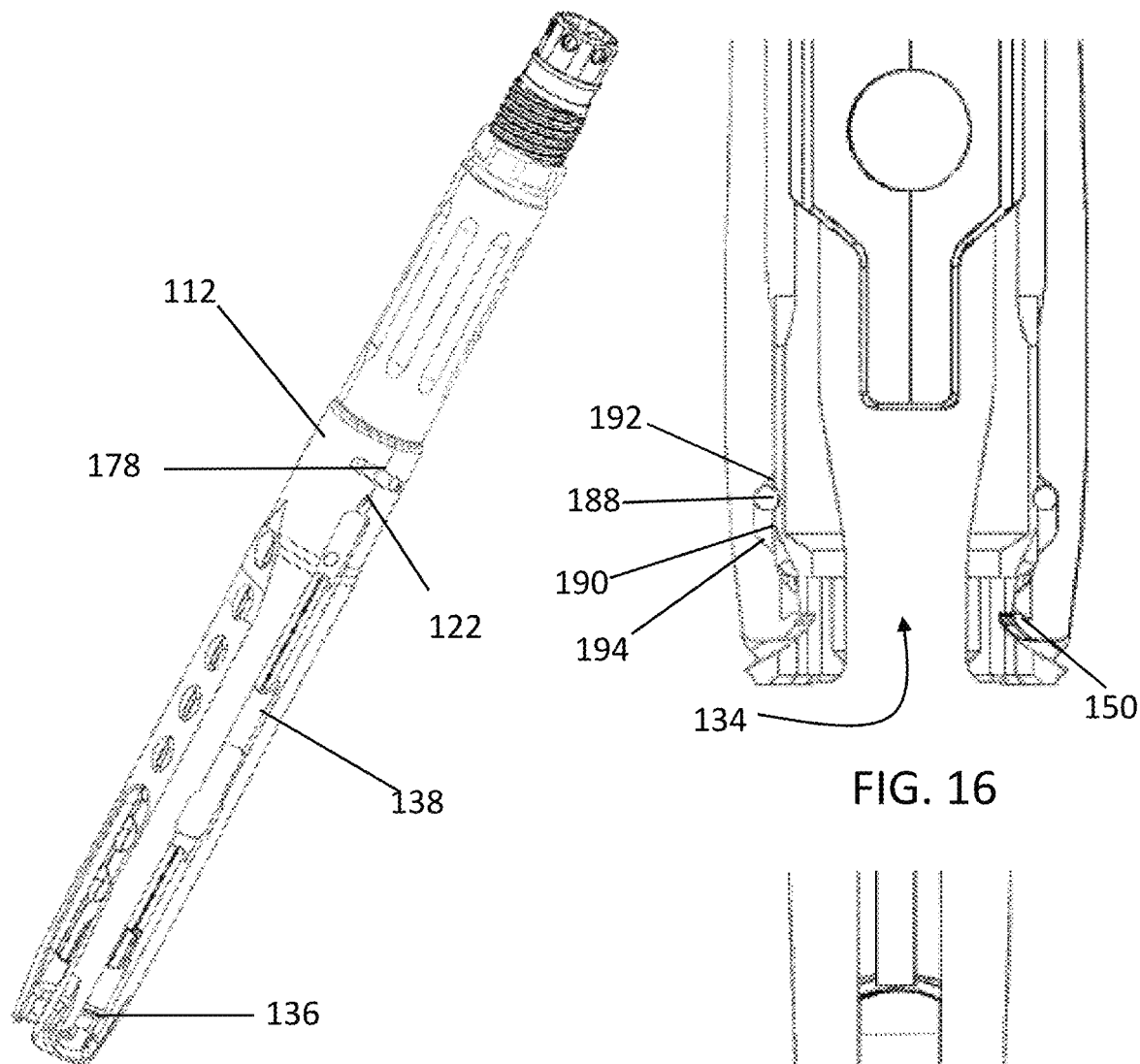

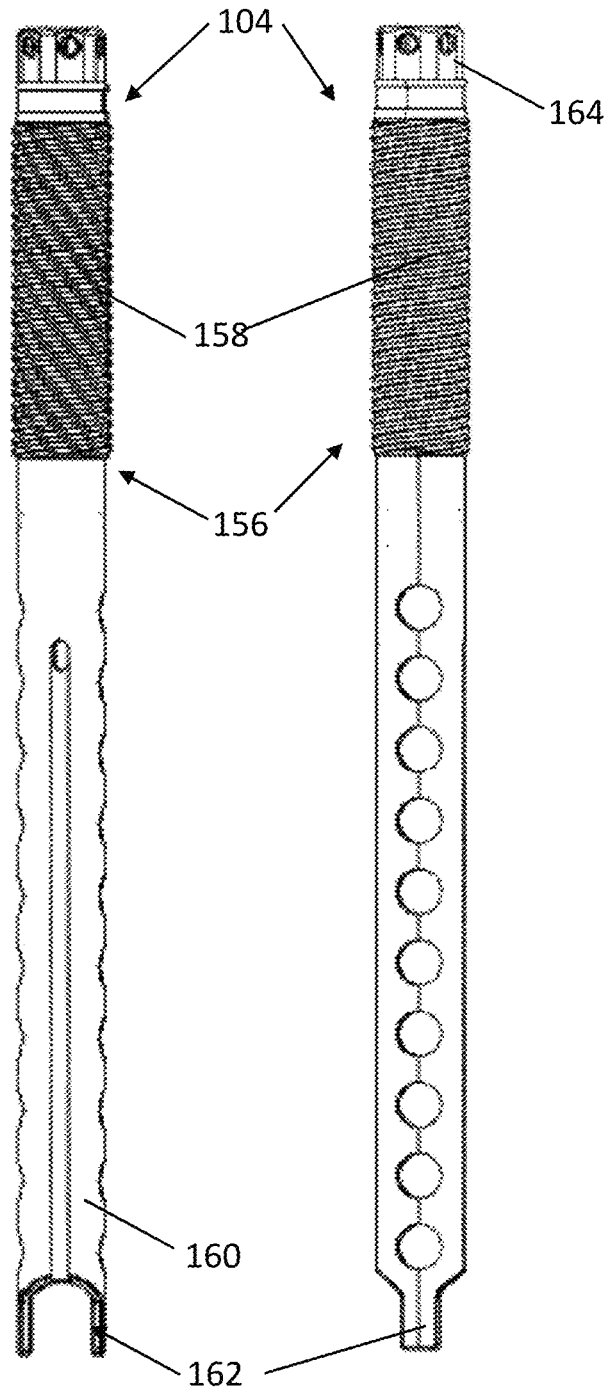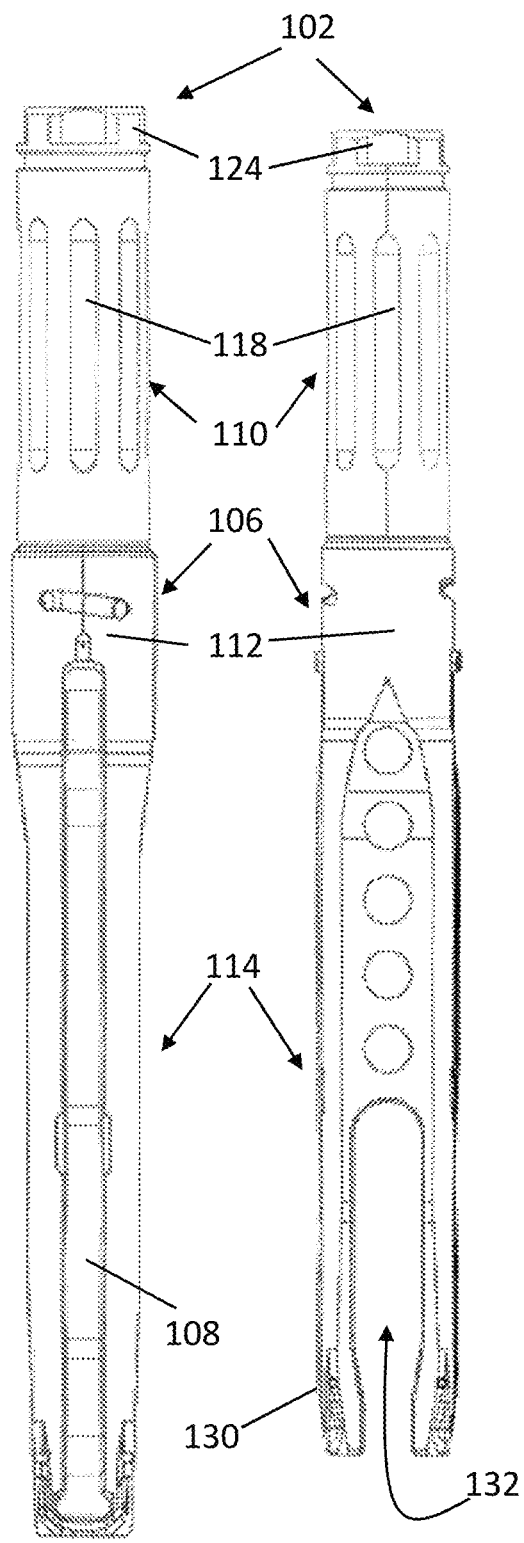
FIG. 18    FIG. 19    FIG. 20    FIG. 21

ROD REDUCTION ASSEMBLIES AND RELATED METHODS

FIELD

The present application relates to the field of spinal surgery and spinal fixation devices, including instruments and associated methods for seating or reducing a spinal fixation rod into a fixation anchor during the installation of a spinal fixation construct.

BACKGROUND

Spinal fixation constructs are utilized to provide stability to the spine. Most often the fixation construct is used as an adjunct to fusion surgery during which adjacent vertebrae are prepared to facilitate bone growth between them. Because motion between the vertebrae tends to inhibit bone growth, the fixation constructs are employed to prevent motion so that bone can grow and achieve a solid fusion. When the position of one or more vertebrae must be adjusted to restore a more natural alignment of the spinal column, the fixation construct also serves to maintain the new alignment until fusion is achieved.

Fixation constructs of various forms are known in the art, of which, rod based fixation constructs are one of the most common. Typically in a rod based construct multiple anchors are coupled to a portion (e.g. the posterior elements) of two or more vertebrae and then connected by a fixation rod. The anchors further include a rod housing in which the fixation rod is captured and locked. The rod housing may be fixed or rotatably coupled to the anchor portion and generally includes a pair of upstanding arms separated by a rod channel. When constructing the fixation construct the surgeon must align and seat the rod in the rod channel of each anchor, an undertaking that is generally referred to as "reduction". Reduction can be a challenge, particularly when one or more of the vertebrae to be connected are out of alignment with other vertebrae, and the reduction distance and force requirements can vary greatly from anchor to anchor. Known rod reduction instruments or reducers, can be bulky, time consuming or frustrating to employ, limited in achievable reduction depth, and other issues that can make them less than desirable. Rod reduction instruments that interlock with the anchor have been described and provide stability to the interaction during the reduction process. Although these reduction tools facilitate a secure interaction between the anchor and the instrument that aids in reduction of the rod, it can be difficult to release the reduction instrument from the anchor in surgical settings where there is limited access, or where the surrounding tissue exerts force against the interface between the instrument and anchor that prevents easy disengagement of the reduction instrument. The rod reduction instrument described herein is directed towards facilitating simple and efficient rod and/or screw manipulation during installation of a fixation construct, and simple disengagement when the manipulation is complete.

SUMMARY

The needs above, as well as others, are addressed by embodiments of a dual rod spinal fixation constructs described in this disclosure.

In a first aspect, a system to facilitate seating of a spinal rod into a rod-receiving portion of a fixation anchor is disclosed, the system comprising a rod reducer with a translation unit and a coupling unit, where the coupling unit is an elongated, generally tubular base with a lumen, a pair of longitudinal recesses on opposite sides of the base member and extending from the central portion to the distal portion, the longitudinal recesses including a displacement feature, a pair of anchor coupling arms located at the distal end of the base member spaced apart to define a cavity and a longitudinal rod channel; a lock mechanism comprising a drive knob; a pair of attachment arms within the longitudinal recesses that including an anchor engagement feature configured to the rod receiving portion of the fixation anchor, an arm displacement feature, and a drive knob engagement feature that engages the drive knob such that rotation of the drive knob results in translation of the attachment arms; and a translation unit including a distal rod engagement end configured to advance in a distal direction relative to the coupling arms, and coupled to a translating mechanism that drives the distal advancement of the distal rod engagement end.

In a second aspect, a system to facilitate seating of a spinal rod into a rod-receiving portion of a fixation anchor is disclosed, the system comprising a rod reducer having a translation unit and a coupling unit, where the coupling unit is an elongated, generally tubular base member with lumen, a pair of multi-pitch helical grooves arranged on opposites sides of the base member, a pair of longitudinal recesses on opposite sides of the base member that extend from the central portion to the distal portion, where the longitudinal recesses include a displacement pin, and a pair of anchor coupling arms spaced apart to define a cavity and a rod channel; a lock mechanism that includes a drive know with a lumen that is sized and configured to slide over the base member and rotate relative to the base member, where the drive knob has a groove along the distal edge of the interior surface and a pair of apertures on opposite sides of the knob with a drive pin passing through and into the lumen to engage the helical grooves of the base member; a pair of attachment arms within the longitudinal recesses that including an anchor engagement feature that engages a fixation anchor, where the attachment arms have an angled recess that engages with the displacement pins of the longitudinal recess and also include a tab that engages the groove of the drive knob such that rotation of the drive knob results in translation of the attachment arms; and a translation unit that includes a rod engagement end that advances in a distal direction relative to the coupling arms and which is coupled to a translating mechanism that drives the distal advancement of the rod engagement end.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 3 is a side view of the example rod reducer of FIG. 1.

FIG. 4 is a front side view of the example rod reducer of FIG. 1.

FIG. 5 is a top view of the example rod reducer of FIG. 1.

FIG. 6 is a bottom view of the example rod reducer of FIG. 1.

FIG. 15 is a perspective view of the rod reducer of FIG. 1 with the attachment arm removed.

FIG. 16 is a front view of the distal end of the rod reducer of FIG. 1.

FIG. 17 is a side view of the distal end of the rod reducer with the attachment arm removed as in FIG. 12.

FIG. 18 is a plan view of a translating unit forming part of the rod reducer of FIG. 1;

FIG. 19 is another plan view of the translating unit of FIG. 15;

FIG. 20 is a plan view of a coupling unit forming part of the rod reducer of FIG. 1;

FIG. 21 is another plan view of the coupling unit of FIG. 17;

DETAILED DESCRIPTION

Figures 1, 2:
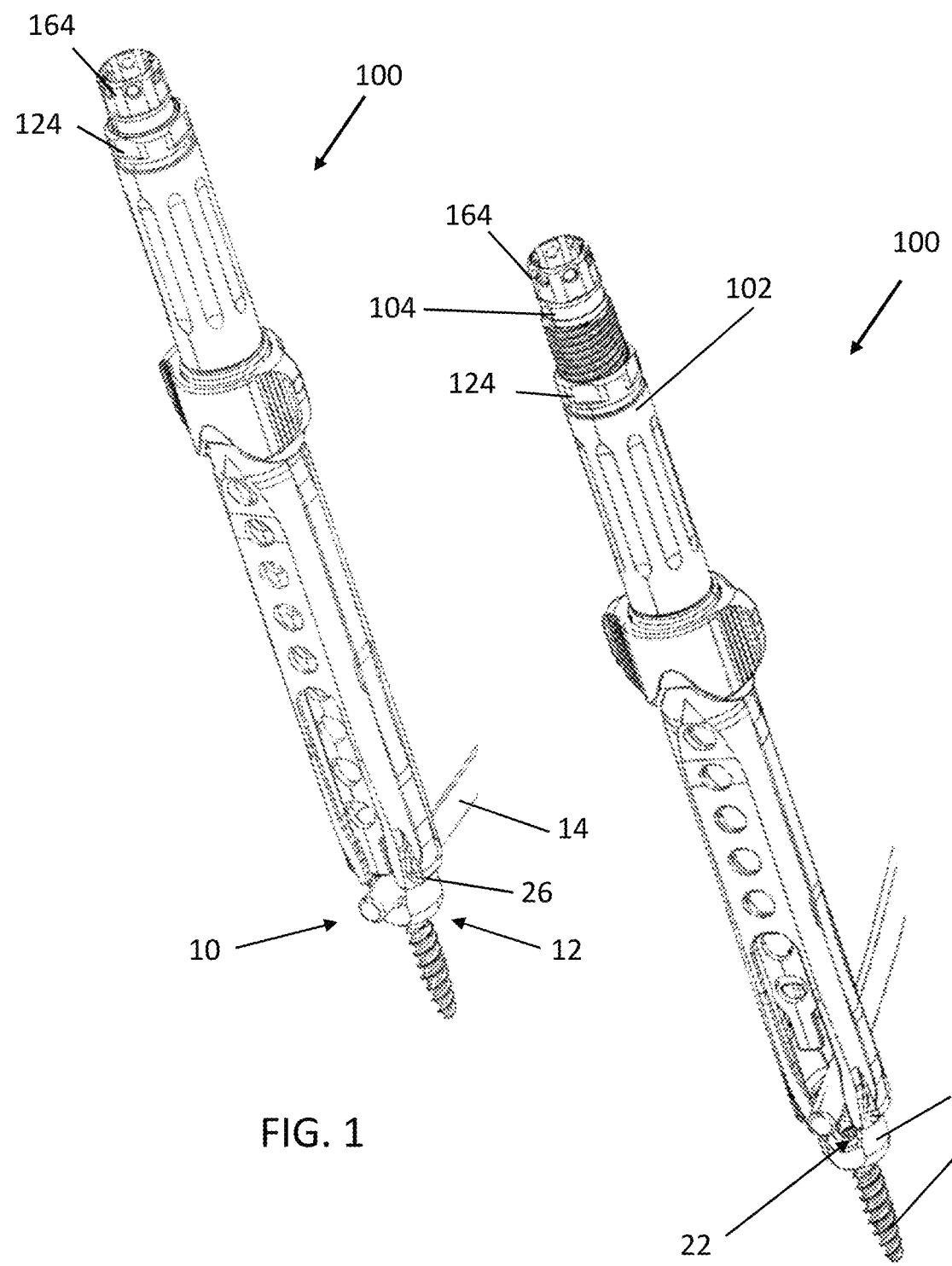
FIG. 1 is a perspective view of a rod reducer for urging a spinal rod to an anchor, according to an example embodiment.
FIG. 2 is an alternative perspective view of the example rod reducer of FIG. 1.

Various example embodiments of devices and techniques for rod reduction during spinal instrumentation procedures are described herein. In the interest of clarity, not all features of an actual implementation are necessarily described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The rod reduction instruments and related implants, instruments and methods described herein boast a variety of inventive features and components that warrant patent protection, both individually and in combination.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The example reduction assembly, or reducer, embodiments described herein are used during the installation of a fixation construct 10 onto the spine of a patient. The fixation construct 10 includes anchor members 12 connected by a fixation rod 14 locked to each anchor 12. An anchor 12 is implanted in each vertebra to be fixed by the construct 10. For example, two anchors 12 may be used to fix two vertebrae together; three may be used to fix three vertebrae together; four may be used to fix four vertebrae together; and so on. The anchor 12 includes a bone anchor 18 and a housing 20 for capturing and locking a fixation rod 14. The bone anchor 18 may be a bone screw suitable for stable fixation to vertebral bone (e.g. pedicle or vertebral body), as shown. The bone anchor 18 may also include other fixation devices (e.g. hooks, staples, clamps, etc. . . . ). The housing 20 has a base that attaches with the bone anchor and a pair of upstanding arms that together form a rod channel 22. The housing also includes a mechanism to lock the fixation rod 14 in position in the rod channel 22. For example, the mechanism may include a locking cap guide and advancement feature disposed on the interior face of each arm that interacts with a complementary feature on a locking cap. The base may be fixed to the anchor 18 or may be coupled such that the housing can rotate in one or more directions (e.g. polyaxial). The housing also includes one or more instrument engagement features for releasably coupling to one or more instruments during implantation. One example of an anchor configured for use with the reducers described herein is shown and described in U.S. patent application Ser. No. 13/456,210, filed Apr. 25, 2012, the entire contents of which are incorporated herein by reference. The reducers described herein can be engaged to one or more of the anchors 12 of the fixation construct 10 to facilitate alignment and advancement of the rod 14 into the rod channel 22 of each anchor.

Now with reference to FIGS. 1-6, a reducer 100 according to one example embodiment is illustrated. The reducer 100 is configured to couple to both arms of anchor 12 and impart a downward force on the rod 14. The downward force on the rod acts to draw the rod and anchor housing 20 together until the rod 14 fully seats in the rod channel 22. A locking mechanism, such as locking cap may then be at least partially engaged to capture the rod 14 in the housing 20 prior to decoupling the reducer 100 from the anchor 12. The reducer 100 includes a coupling unit 102 that connects to the anchor 12 and a translation unit 104 that translates relative to the coupling unit 102 to urge the rod 14 towards the anchor.

Figure 7:
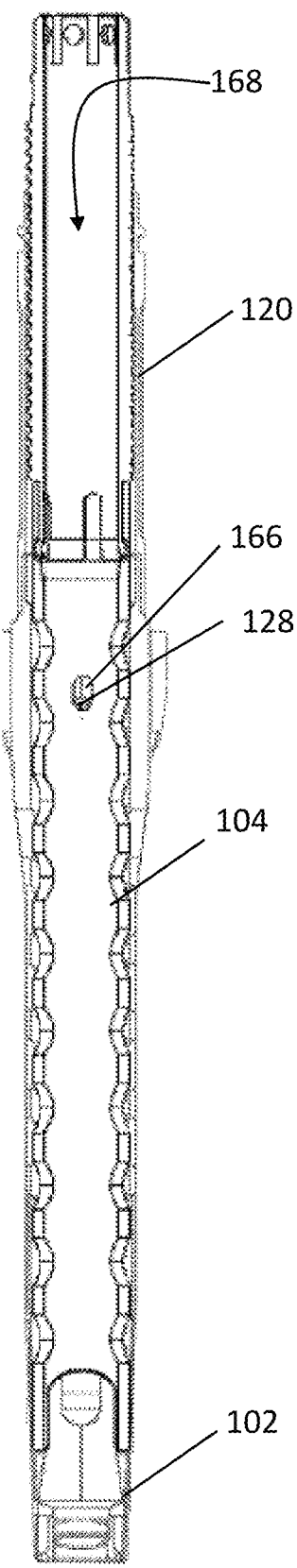
FIG. 7 is a cross-section view of the rod reducer of FIG. 1.
Figure 8:
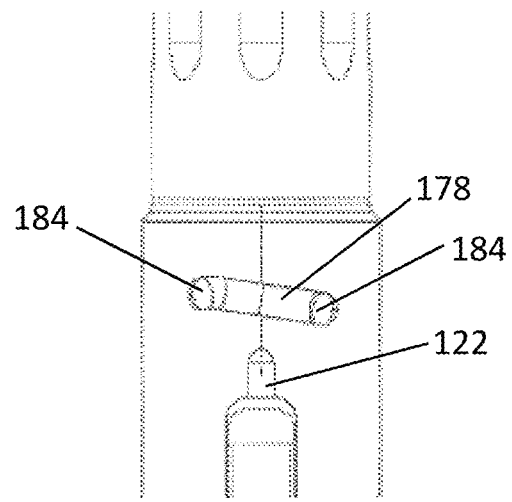
FIG. 8 is a perspective view of the lock mechanism according to an example embodiment with the drive knob removed.
Figure 9:
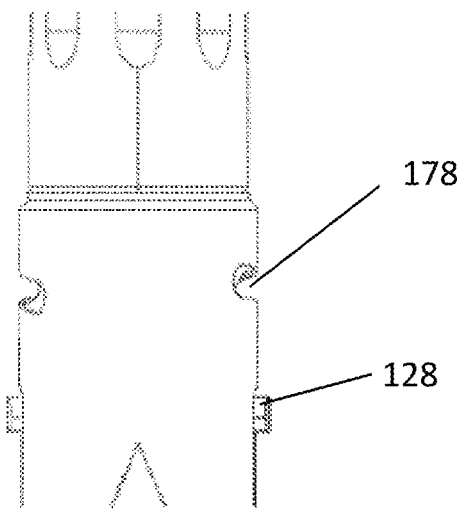
FIG. 9 is an alternative perspective view of the lock mechanism of FIG. 8.
Figure 10:
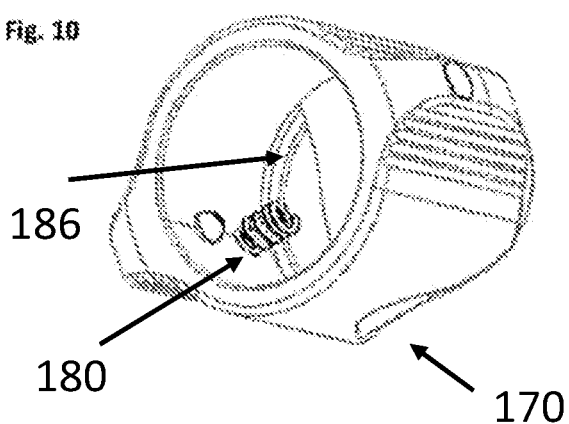
FIG. 10 is a perspective view of a drive knob of the example rod reducer of FIG. 1.
Figure 11:
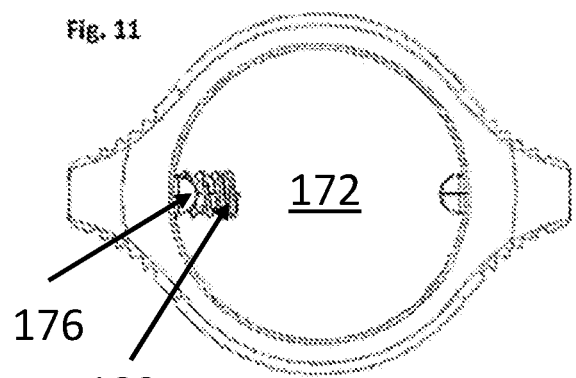
FIG. 11 is a top view of the drive knob of FIG. 7.
Figure 12:
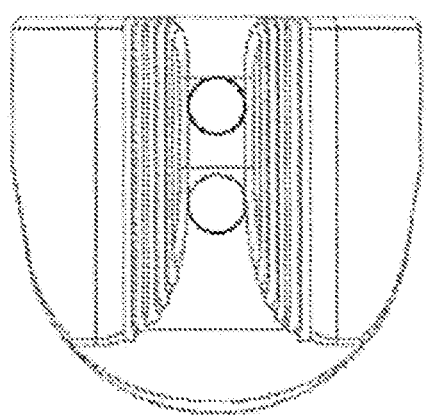
FIG. 12-13 are side views of the drive knob of FIG. 7.
Figure 13:
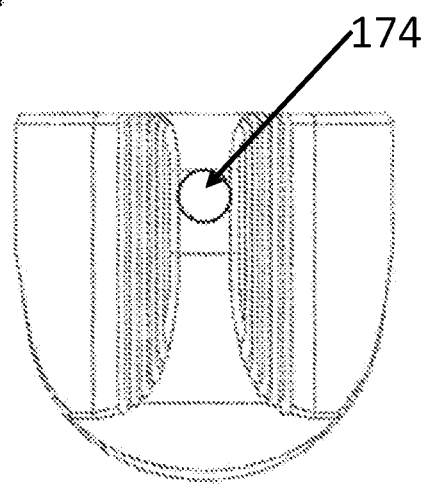
Figure 14:
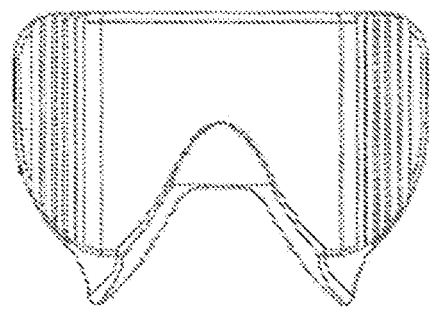
FIG. 14 is a front view of the drive knob of FIG. 7.

The coupling unit 102 includes a base member 106 and first and second attachment arms 108 that are pivotally coupled with the base member 106. The base member 106 is an elongated, generally tubular member having a proximal portion 110, a central portion 112, a distal portion 114, and a central lumen 116 extending longitudinally through the entire length of the base member 106. The proximal portion 110 includes a handle 118 that provides a gripping area for a user to grip the reducer 100. Above the grip is a head 124 that allows the coupling of other instruments with the reducer 100. The head 124 may be configured to mimic the proximal end of minimally invasive screw guides such that any instruments that engage or couple with the guides may also engage or couple with the reducer 100 (for example, vertebral body derotation assemblies, counter torques, etc. . . . ). As shown in FIG. 7, the proximal portion 110 further includes a threaded portion 120 formed on the interior of the proximal portion 110 (i.e. the proximal end of the lumen 116) for threadedly engaging the translating unit 104. Between the proximal portion 110 and the central portion 112 is drive knob 170. As shown in FIG. 15, the central portion 112 includes a pair of lateral recesses 122 positioned opposite one another on either side of the base member 106. Each lateral recess 122 is adapted to receive a proximal end 142 of one attachment arm 108. Guide pins 128 are located within the lateral recesses 122 and extend into the lumen 116. The guide pins 128 engage the guide slots 166 of the translation unit 104 to ensure that the pusher member 160 of the translation unit 104 does not rotate during reduction. The distal portion 114 includes a pair of anchor coupling arms 130 extending distally from the central portion of the base. The anchor coupling arms 130 are separated by a channel 132 that aligns with the anchor rod channel 22 when the reducer 100 is coupled to the anchor 12. To couple to the anchor 12, a cavity 134 at the distal end of the coupling arms 130 is dimensioned to snugly receive the arms of the anchor housing 20 therein. The distal portion 114 further includes a pair of lateral openings 136 positioned opposite one another near the distal end of the base member 106. The lateral openings 136 are adapted to allow passage of the distal ridge 150 of the attachment arm 108 to enable the distal ridge 150 to engage the housing 20. As shown in FIG. 15, a pair of longitudinal recesses 138 is positioned on opposite sides of the base member 106 and extend from the central portion 112 to the distal portion 114, and more specifically from the lateral recesses 122 to the lateral openings 136. Each longitudinal recess 138 is dimensioned to receive the length of the attachment arm 108 therein which helps reduce the lateral profile of the reducer 100. As shown most clearly in FIG. 16, each longitudinal recess 138 includes a displacement feature 188 that extends from the sidewall of the recess 138. The displacement feature 188 may be a pin, or a ramp, or any other means known in the art for exerting an outward force on the attachment arms 108 as described further below.

As shown in FIGS. 10-14, the drive knob 170 has a generally cylindrical internal contour and a lumen 172 sized and configured to slideably receive the base member 106 therein and allow rotation of the knob 170 relative to the base member 106. The drive knob 170 includes an internal circumferential groove 186 along the wall of the lumen 172, near the distal end of the knob 170. The internal groove 186 interacts with the attachment arms 108 as described more fully below. The drive knob has one or more drive pin apertures 174. A drive pin 176 passes through the aperture and extends into the lumen 172 of drive knob 170. The drive pin 176 interacts with a multi-pitch helical groove 178 on the base member 106. The interaction between the drive pin 176 and the helical groove 178 of the base member 106 serves to connect the drive knob 170 to the base member 106, preventing the drive knob 170 from sliding off of the base member 106. The drive pin 176 also servers to allow the rotation of the drive knob 170 within a specific range of movement prescribed by the length of the helical groove 178. When the drive knob 170 is rotated, the interaction between the drive pin 176 and helical groove 178 of the base member 106 results in both rotation and translation of the drive knob 170 relative to the base member 106. The instrument may have one interacting drive pin and helical groove, or there may be multiple drive pin and helical groove pairings for increased stability.

The drive knob also may include a lock aperture 180. Within the lock aperture is a spring-loaded ball-bearing lock 182 that extends into the lumen 172. The ball-bearing lock 182 may interact with one or more longitudinal lock grooves 184 on the base member 106 to create a soft stop when the drive knob in rotational position aligned with one of the grooves 184. The longitudinal lock grooves may correspond to any one of a load position, lock position, or unlock position. In the load position, the drive knob 170 is rotated such that the drive pin 176 is at a mid-point of the helical groove 178. In the lock position, the drive knob 170 is rotated so that the drive pin 176 is at the most proximal position of the helical groove 178. In the unload position, the drive knob 170 is rotated so that the drive pin 176 is at the most distal position of the helical groove 178. When the drive knob is in the load position, the spring-loaded ball bearing may be located in a corresponding longitudinal lock groove. As a user rotates the drive knob 170, the spring-loaded ball bearing will contact the side of the longitudinal groove and the force will compress the spring-loaded ball bearing lock 182 allowing the drive knob 170 to rotate relative to the base member 106. When the lock or unload position is reached, the spring-loaded ball bearing lock 182 will engage the corresponding longitudinal lock groove 184. The force of the spring-loaded ball-bearing lock interacting with the longitudinal lock groove 184 will maintain the drive knob 170 in position until the user applies further rotational force. The engagement of the spring-loaded ball bearing lock 182 with the longitudinal lock grooves 184 may provide a tactile signal to the user that the drive knob is in the desired position. Visual lock status indicators (not shown) may be included to indicate the position of the drive knob.

Figure 22:
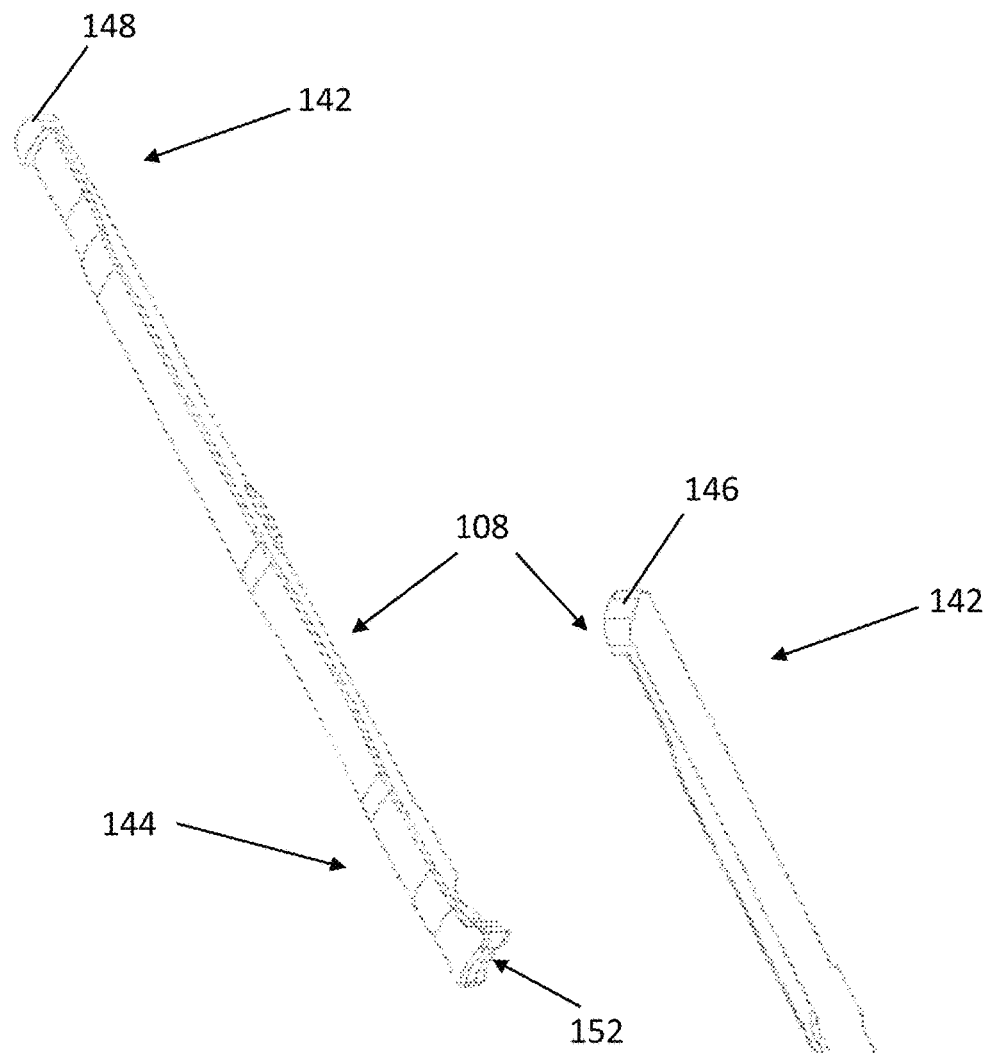
FIG. 22 is a front side view of an attachment arms forming part of the coupling unit of FIG. 1.
Figure 23:
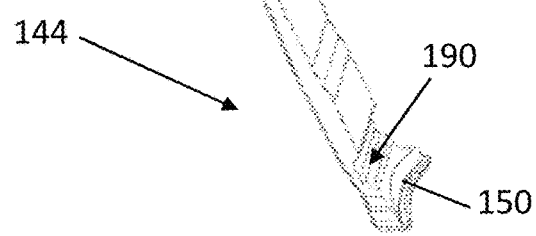
FIG. 23 is a back side view of an attachment arms forming part of the coupling unit of FIG. 1.

The first and second attachment arms 108 extend from the central portion 112 to the distal portion 114 along the lateral exterior of the base member 106, and are positioned within longitudinal recesses 138. FIGS. 22-23 illustrate an attachment arm 108 in greater detail. Although described with reference to a single attachment arm 108, it is to be understood that each attachment arm 108 is identical. By way of example, each attachment arm 108 is an elongated member having a proximal end 142, a distal end 144, and a pivot 146. The proximal end 142 includes a tab 148 configured to interact with the circumferential groove 186 of the drive knob 170. The tab 148 is slideably fitted into the circumferential groove 186 of the drive knob 170. This interaction allows the drive knob 170 to rotate relative to the attachment arms 108, while maintaining the attachment arms 108 and drive knob 170 in a longitudinally fixed position relative to one another. When the drive knob 170 is rotated, both the drive knob 170 and the attachment arms 108 are translated relative to the base member 106, but only the drive knob 170 rotates relative to the base member 106. The distal end 144 of the attachment arm includes a distal ridge 150 that extends through the lateral opening 136 in the base member 106 and into the cavity 134 to engage the engagement features 26 of the housing 20. Each distal ridge 150 has a distal-facing tapered surface 152 that is inwardly tapered. Just proximal to the distal ridged 150 is an angled recess 190 that interacts with the displacement feature 188 of the longitudinal recess 138 of the base member 106. When the drive pin 176 is in the load or lock position, the displacement feature 188 is located within the space of the angled recess 190, between the proximal face 192 and distal face 194 of the angled recess 190. When the drive knob 170 is rotated to the unload position, the proximal face 192 of the angled recess 190 will contact the displacement feature 188. In this position, the displacement feature 188 exerts an outward force on the attachment arm 108 pushing the attachment arms apart to promote disengagement from the anchor.

When the drive knob 170 is rotated to the load position, the angled recess 190 is not in contact with the displacement feature 188. The attachment arm 108 is free to flex as the distal-facing tapered surface 152 automatically pushes the distal end 144 of the attachment arm 108 outward as the arms of the housing 20 are advanced into the cavity 134, permitting the ridges 150 to pass the tops of the housing arms until they engage the anchor features 26. The natural flexibility of the attachment arms 108 causes them to flex inward when the distal ridges 150 encounter the anchor features 26 and the outward pressure is released. This way, the reducer 100 can be positioned over the rod 14 and quickly snapped onto and engaged with the anchor with the simple application of downward pressure. To secure the engagement of ridges 150 into the anchor features 26, and hence, the reducer 100 to the housing 20, the user rotates the drive knob 170 into the lock position. Rotation of the drive knob 170 causes the drive pin 176 to move within the allotted distance of the multi-pitch helical groove 178 and results in the translation of the attachment arms 108 in a proximal direction to snug the interaction between the distal ridges 150 and the anchor features, removing any gap between them. During rotation of the drive knob 170, the spring-loaded ball bearing lock 182 may be rotated from a longitudinal lock groove 184 corresponding to the load position into a longitudinal lock groove 184 corresponding to the lock position, providing a tactile signal when the attachment arms 108 have been fully translated in the proximal direction, and the distal ridges 150 of the attachment arms 108 are in secure engagement with the anchor features 26.

To disengage the rod reducer 100 from the anchor 18, the user may rotate the drive knob 170 in the opposite direction to translate the attachment arms 108 distally. As the drive knob 170 is rotated, the drive pin 176 moves through the multi-pitch helical groove 178 past the center load position, into the distal-most unload position. As the attachment arms 108 are translated distally, the angled recess 190 of the attachment arm 108 contacts the displacement feature 188 in the longitudinal recess 138. Interaction of the angled proximal edge 192 of the angled recess with the displacement feature 188 causes the distal end of the attachment arm to be forced outward, increasing the distance between the attachment arms 108. The outward force on the attachment arms 108 caused by interaction of the displacement feature 188 with the angled recess 190 counteracts resistance that may be caused by local tissue or a narrow surgical access window and actively promotes disengagement of the ridges 150 from the engagement features 26. The reducer 100 may then be removed.

As shown in FIGS. 18-19, the translation unit 104 includes a shaft 156 capped with a drive nut 164 at the proximal end and a pusher member 160 ending in a pair of reduction arms 162 at the distal end. The reduction arms 162 are situated between the coupling arms 130 and align with the channel 132 on each side. The distal ends of reduction arms 162 will contact the rod and may be configured with a shape (e.g. concave) to complement the contour of the rod 14. Along the shaft 156 between the drive nut 164 and pusher member 160 is a threaded region 158 with threading complementary to the inner threading 120 of the base member 106 to translate the translation unit 104 relative to the coupling unit 102 upon rotation of the shaft 156. The drive nut 164 can be engaged by a handle (not shown) to facilitate rotation. The pusher member 160 is coupled to the threaded shaft 156 in such a way that the pusher member and shaft are fixed longitudinally but freely rotatable relative to each other. Though not shown, the threaded region may include multiple flexible fingers, each having a ridge that is received in an internal groove of the pusher member 160.

The pusher member further includes a pair of guide slots 166 is positioned opposite one another on either side of the shaft 156 and extend proximally along the pusher member 160. The guide slots 166 are dimensioned to receive the guide pins 128 therein to prevent rotation of the pusher member 160 when the threaded portion 158 is rotated. A passage 168 extends through the translation unit 104 from the drive nut 164 to reduction arms 162 to receive locking cap and a driver therethrough to engage the locking cap to the housing 20 prior to removing the reducer 100. Alternatively, the translation unit 104 may further be configured to carry a preloaded locking cap, for example, as described and illustrated with respect to reducer 100.

According to one exemplary embodiment, the rod reducer includes a translation unit and a coupling unit. The coupling unit includes an elongated, generally tubular base member with a proximal, central, and distal portion. The coupling unit has a lumen extending longitudinally therethrough from the proximal to the distal portion. The coupling unit also includes a pair of longitudinal recesses positioned on opposite sides of the base member and extending from the central portion to the distal portion. The longitudinal recesses include a displacement feature. In some embodiments, the displacement feature extends from the sidewall of the longitudinal recess into its lumen. In some embodiments the displacement feature is a pin. In other embodiments, the displacement feature may be a ramp. The longitudinal recesses also include a pair of anchor coupling arms located at the distal end of the base member, the coupling arms are spaced apart to define a cavity and a longitudinal rod channel between them. In some embodiments, the base member also includes one or more multi-pitch helical grooves on the central portion of the base. In some embodiments, the base member may include one or more longitudinal lock grooves that correspond to one or more of a load, lock, or unload position. In some embodiments, the base member may include a visual lock status indicator of the load, lock, or unload position.

The reducer further includes a lock mechanism located between the central portion and proximal portion of the base member. The lock mechanism includes a drive knob. The drive knob has a generally cylindrical internal contour and a lumen. The drive knob is sized and configured to slideably receive the base member and allow rotation of the knob relative to the base member. In some embodiments, the drive knob includes a pair of apertures with drive pins passing therethrough and into the lumen. In such embodiments, the drive pins engage with the helical grooves of the base member. In some embodiments, the drive knob includes a circumferential groove along a distal edge of the surface of the lumen. In some embodiments, the drive knob includes a spring-loaded ball bearing lock that reversibly interacts with the longitudinal lock grooves on the base.

The reducer includes a pair of attachment arms that extend from the central portion to the distal portion of the base member and are positioned within the longitudinal recesses, the attachment arms include an anchor engagement feature at the distal end that is configured to engage complementary engagement features on the rod receiving portion of the fixation anchor. The attachment arms include an arm displacement feature that is configured to engage with the displacement feature of the longitudinal recesses. In some embodiments the displacement feature is an angled recess. The attachment arms also include a drive knob engagement feature at their proximal end. The drive knob engagement feature engages complementary feature on the drive knob such that rotation of the drive knob in a first direction results in proximal translation of the attachment arms and rotation of the drive knob in a second direction results in distal translation of the attachment arms. In some embodiments, the drive knob engagement feature is a tab that slideably fits within the circumferential groove of the drive knob. The engagement between the attachment arms and the drive knob allows translation of the arms with the knob, but the attachment arms do not rotated relative to the base member.

The translation unit includes a distal rod engagement end that is configured to advance in a distal direction relative to the coupling arms. The distal rod engagement end is coupled to a translating mechanism that drives the distal advancement of the distal rod engagement end.

In practice, anchors 12 are implanted in each of the vertebra to be fixed, and the rod 14 is inserted into the anchor housings. The drive knob 170 is rotated to the load position. The distal ends of the coupling arms 130 are advanced over the rod such that the rod 14 is captured in the channel 132 and onto the anchor housing 20 until the attachment arms 108 engage the features 26 on the housing. The user then rotates the drive knob 170 to the lock position to pull the attachment arms proximally and secure the interaction between the attachment arms 108 and the engagement features 26 of the anchor. The user then attaches a handle or other suitable tool to the drive nut 164 of the translation unit 104. The user then rotates the handle (or other tool), causing the threaded region 158 of shaft 156 to advance distally through the threaded portion 120 of the coupling unit 102. This in turn causes the translation unit 104 as a whole to advance along the coupling unit 102 with a downward force, thereby advancing the rod 14 until the rod is fully seated in the housing 20. After the rod 14 is fully seated in housing 20 a locking cap can be engaged with the locking engagement feature to capture and lock the rod 14 to the anchor 12. To disengage the reducer 100 from the housing 20, the user rotates the drive knob 170 to the unload position to move the attachment arms 108 distally to disengage them from the anchor. This will cause the distal ends 144 to be pushed outward by the displacement features 188 and disengage the ridges 150 from the housing 20. The reducer 100 may then be removed.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. A system to facilitate seating of a spinal rod into a rod-receiving portion of a fixation anchor, comprising:
   a rod reducer having a translation unit and a coupling unit, the coupling unit comprising:
      an elongated, generally tubular base member with a proximal, central, and distal portion, a lumen extending longitudinally therethrough, a pair of longitudinal recesses positioned on opposite sides of the base member and extending from the central portion to the distal portion, the longitudinal recesses including a displacement feature, and a pair of anchor coupling arms located at a distal end of the base member, the coupling arms being spaced apart to define a cavity and a longitudinal rod channel therebetween, the coupling arms configured for coupling to a housing of the fixation anchor, wherein each of the pair of longitudinal recesses is located on a corresponding coupling arm of the pair of anchor coupling arms;
      a lock mechanism comprising a drive knob located between the central portion and proximal portion of the base member;
      a pair of attachment arms extending from the central portion to the distal portion of the base member and positioned within the longitudinal recesses, the attachment arms including an anchor engagement feature at the distal end configured to engage complementary engagement features on the rod receiving portion of the fixation anchor the attachment arms each including an arm displacement feature configured to engage with the displacement feature of each longitudinal recess, the attachment arms also including a drive knob engagement feature at a proximal end that engages a complementary feature on the drive knob and wherein rotation of the drive knob results in translation of the attachment arms;
      the translation unit including a distal rod engagement end configured to advance in a distal direction relative to the coupling arms, the distal rod engagement end being coupled to a translating mechanism that drives the distal advancement of the distal rod engagement end.

2. The system of claim 1, wherein the drive knob has a generally cylindrical internal contour and a lumen therethrough, sized and configured to slideably receive the base member therein and allow rotation of the knob relative to the base member.

3. The system of claim 1, wherein the base member further comprises a multi-pitch helical groove on the central portion of the base member.

4. The system of claim 3, wherein the drive knob comprises an aperture on the knob, with a drive pin passing therethrough and into the lumen of the drive knob to engage the helical groove of the base member.

5. The system of claim 4, wherein the drive knob further comprises a groove along a distal edge of an interior surface and the knob engagement feature of the attachment arms comprises a tab configured to slideably interact with the groove, to allow the knob to rotate about its longitudinal axis relative to the attachment arms while the attachment arms translate along the longitudinal axis with the knob.

6. The system of claim 1, wherein the attachment arm displacement feature is an angled recess near the distal end of the attachment arm and the displacement feature of the longitudinal recess is a pin in a sidewall of each longitudinal recess.

7. The system of claim 6, wherein rotation of the drive knob causes translation of the attachment arm in a distal direction and contact between the angled recess and the pin exerts a force to push the attachment arms apart to an unload position.

8. The system as in claim 1, wherein base member further comprises one or more positional lock grooves, and the drive knob comprises a spring-loaded ball bearing lock, wherein the ball bearing lock reversibly engages the lock groove when the drive knob is rotated.

9. The system of claim 8, wherein the one or more positional lock grooves correspond to the load position lock position, or unlock position.

10. The system of claim 8, wherein the one or more positional lock grooves are longitudinal grooves on the base member.

11. The system of claim 1 wherein rotation of the drive knob in a first direction translates the attachment arms in a proximal direction to lock the reduction tool to the fixation anchor.

12. The system of claim 6, wherein rotation of the drive knob in a second direction opposite the first causes translation of the attachment arm in a distal direction and contact between the angled recess and the pin exerts a force to push the attachment arms apart to an unload position.

13. The system as in claim 1, further comprising a visual lock status indicator.

14. The system of claim 1, wherein the distal rod engagement end of the translation unit comprises a pair of opposing reduction arms situated between the coupling arms, the pair of opposing reduction arms separated by a guide slot that aligns generally with the longitudinal rod channel.

15. The system of claim 14, wherein the translation unit comprises a threaded shaft proximal to the pair of opposing reduction arms, and wherein the threaded shaft and the pair of opposing reduction arms are longitudinally fixed but rotatable relative to each other.

16. The system of claim 1, wherein the pair of longitudinal recesses extends from an outer surface of the pair of anchor coupling arms.

17. A system to facilitate seating of a spinal rod into a rod-receiving portion of a fixation anchor, comprising:
a rod reducer having a translation unit and a coupling unit, the coupling unit comprising:
an elongated, generally tubular base member with a proximal, central, and distal portion, a lumen extending longitudinally therethrough, a pair of multi-pitch helical grooves arranged on opposites sides of the central portion of the base member, a pair of longitudinal recesses positioned on opposite sides of the base member and extending from the central portion to the distal portion, the longitudinal recesses including a displacement pin, and a pair of anchor coupling arms located at a distal end of the base member, the coupling arms being spaced apart to define a cavity and a rod channel therebetween, the coupling arms configured for coupling to a housing of the fixation anchor, wherein each of the pair of longitudinal recesses is located on a corresponding coupling arm of the pair of anchor coupling arms;
a lock mechanism comprising a drive knob located between the central portion and proximal portion of the base member, wherein the drive knob is generally cylindrical with a lumen therethrough, sized and configured to slideably receive the base member therein and allow rotation of the knob relative to the base member, the drive knob having a groove along a distal edge of an interior surface and a pair of apertures on opposite sides of the knob, each with a drive pin passing therethrough and into the lumen of the drive knob to engage the helical grooves of the base member;
a pair of attachment arms extending from the central portion to the distal portion of the base member and positioned within the longitudinal recesses, the attachment arms including an anchor engagement feature at the distal end that engages complementary engagement features on the rod receiving portion of the fixation anchor, the attachment arms each including an angled recess that engages with the displacement pin of each longitudinal recess, the attachment arms also including a tab at a proximal end that engages the groove of the drive knob, wherein rotation of the drive knob results in translation of the attachment arms;
the translation unit including a distal rod engagement end that advances in a distal direction relative to the coupling arms, the distal rod engagement end being coupled to a translating mechanism that drives the distal advancement of the distal rod engagement end.

18. The system of claim 17, wherein the distal rod engagement end of the translation unit comprises a pair of opposing reduction arms situated between the coupling arms, the pair of opposing reduction arms separated by a guide slot that aligns generally with the longitudinal rod channel.

19. The system of claim 18, wherein the translation unit comprises a threaded shaft proximal to the pair of opposing reduction arms, and wherein the threaded shaft and the pair of opposing reduction arms are longitudinally fixed but rotatable relative to each other.

20. A system to facilitate seating of a spinal rod into a rod-receiving portion of a fixation anchor, comprising:
a rod reducer having a translation unit and a coupling unit, the coupling unit comprising:
an elongated, generally tubular base member with a proximal, central, and distal portion, a lumen extending longitudinally therethrough, a pair of longitudinal recesses positioned on opposite sides of the base member and extending from the central portion to the distal portion, the longitudinal recesses including a displacement feature, and a pair of anchor coupling arms located at a distal end of the base member, the coupling arms being spaced apart to define a cavity and a longitudinal rod channel therebetween, wherein the base member comprises a multi-pitch helical groove on the central portion thereof;
a lock mechanism comprising a drive knob located between the central portion and proximal portion of the base member, wherein the drive knob comprises an aperture thereon, with a drive pin passing therethrough and into the lumen of the drive knob to engage the multi-pitch helical groove of the base member;
a pair of attachment arms extending from the central portion to the distal portion of the base member and positioned within the longitudinal recesses, the attachment arms including an anchor engagement feature at the distal end configured to engage complementary engagement features on the rod receiving portion of the fixation anchor the attachment arms each including an arm displacement feature configured to engage with the displacement feature of each longitudinal recess, the attachment arms also including a drive knob engagement feature at a proximal end that engages a complementary feature on the drive knob and wherein rotation of the drive knob results in translation of the attachment arms;

the translation unit including a distal rod engagement end configured to advance in a distal direction relative to the coupling arms, the distal rod engagement end being coupled to a translating mechanism that drives the distal advancement of the distal rod engagement end.

* * * * *